US005489270A

United States Patent [19]
van Erp

[11] Patent Number: 5,489,270
[45] Date of Patent: Feb. 6, 1996

[54] CONTROLLED FLEXIBLE CATHETER

[75] Inventor: Wilhelmus P. M. M. van Erp, Oldenoert, Netherlands

[73] Assignee: Cordis Corporation, Miami Lakes, Fla.

[21] Appl. No.: 257,806

[22] Filed: Jun. 10, 1994

[30] Foreign Application Priority Data

Jun. 11, 1993 [NL] Netherlands ............ 9301018

[51] Int. Cl.$^6$ ............ A61M 37/00
[52] U.S. Cl. ............ 604/95; 604/282; 128/772
[58] Field of Search ............ 604/95, 282, 280; 128/772, 656–658

[56] References Cited

U.S. PATENT DOCUMENTS

| | | |
|---|---|---|
| 3,470,876 | 10/1969 | Barchilon ............ 604/95 |
| 3,625,200 | 12/1971 | Muller . | |
| 4,960,134 | 10/1990 | Webster, Jr. ............ 128/786 |
| 5,125,896 | 6/1992 | Hojeibane ............ 604/95 |
| 5,176,126 | 1/1993 | Chikama ............ 604/282 X |
| 5,199,950 | 4/1993 | Schmitt et al. ............ 604/95 |

FOREIGN PATENT DOCUMENTS

| | | |
|---|---|---|
| 66120 | 5/1982 | European Pat. Off. . |
| 306010 | 3/1989 | European Pat. Off. . |
| 361314 | 4/1990 | European Pat. Off. . |
| 304724 | 3/1993 | WIPO . |

OTHER PUBLICATIONS

European Search Report No. EP 9420 1603, dated 7, Sep. 1994.

*Primary Examiner*—John D. Yasko
*Attorney, Agent, or Firm*—Lockwood, Alex, Fitzgibbon & Cummings

[57] ABSTRACT

The invention relates to a catheter having a tube-like basic body with a distal end and a proximal end provided with a connecting member, at least one continuous channel and a flexible part at the distal end. In the flexible end section a pull wire, extending through the channel to the outside of the proximal end, can be attached eccentrically. The end section preferably includes an eccentrically positioned channel through which the pull wire or other bending member extends. The pull wire can be doubled back in a hook-shaped fashion at its end and the bent end-piece incorporated in a substantially diametrically opposite, eccentrically situated cavity. With a preferred embodiment the deflection of the end section can be varied with the aid of a sliding wire advanced further or less far in the end section. Also, a strip-like, longitudinally extending electrode of a helically wound coil can be included.

26 Claims, 4 Drawing Sheets

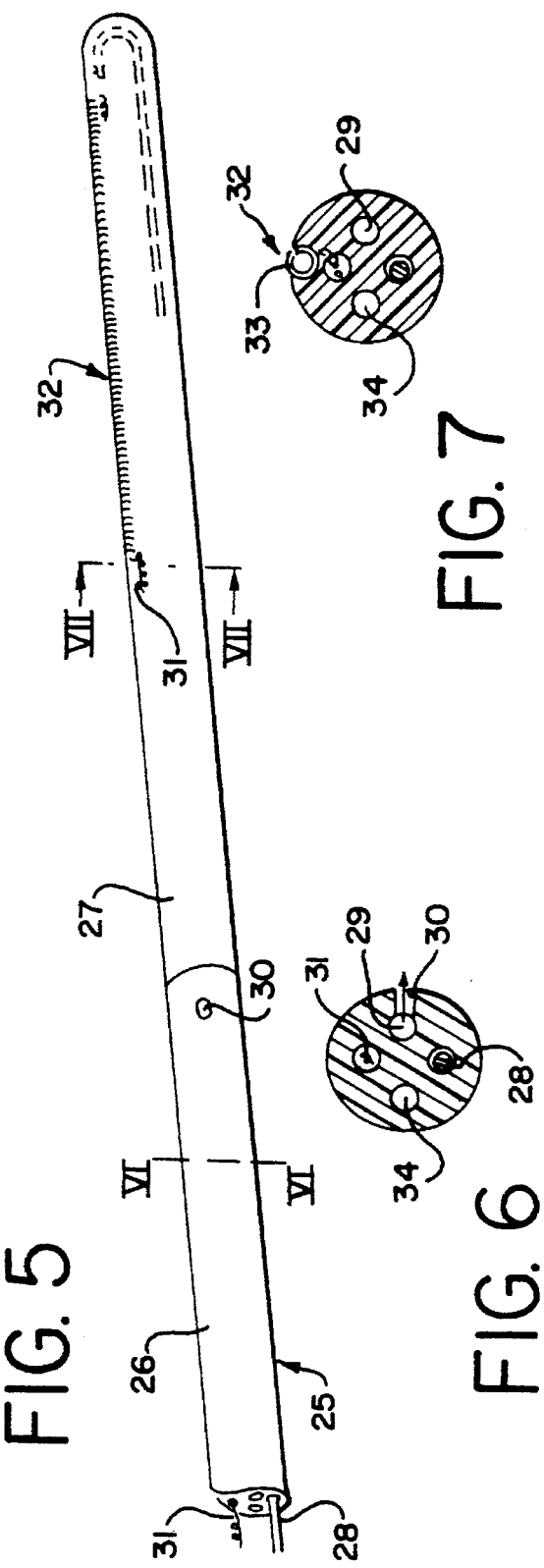
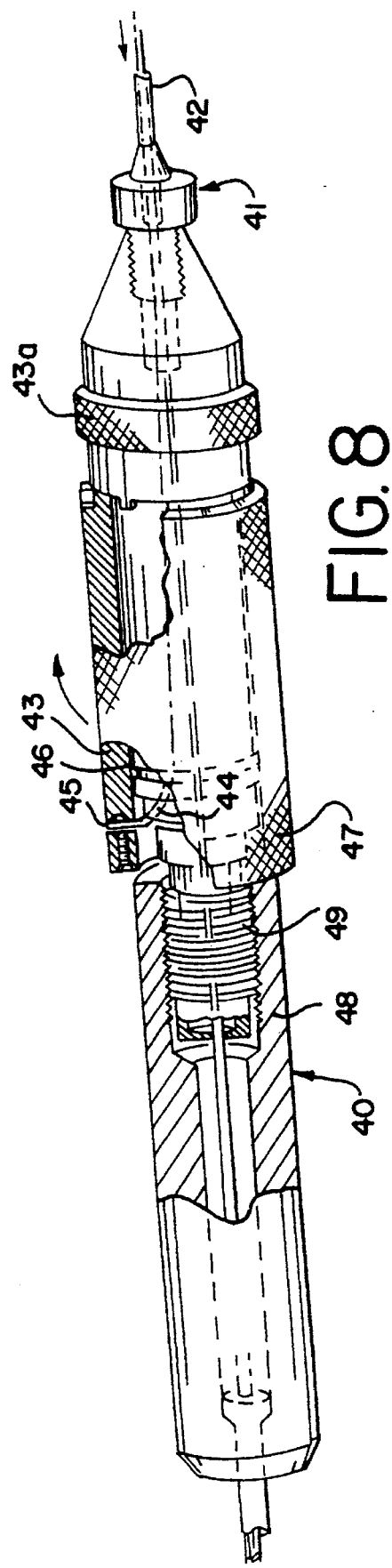

CONTROLLED FLEXIBLE CATHETER

BACKGROUND AND DESCRIPTION OF THE INVENTION

The invention generally relates to a catheter, more particularly to a catheter for angiographic uses. Included is a tube-like basic body with a distal end and a proximal end for connection to a proximal end hub or the like for grasping, manipulating and controlling the catheter. At the proximal end, the catheter is provided with a flexible portion which, when in use, can be bent in a controlled manner from the proximal end. The catheter can also include a strip-like electrode which is a helically wound wire.

In order to bend the distal end portion of a catheter in a controlled manner, it is known to make use of a guidewire with a tip bent in a specific shape which is advanced to the end portion by way of the channel of the catheter. By rotation or lengthwise shifting of the guidewire in relation to the catheter, a deflection of the end-section is achieved. In that respect, the deflection can be oriented in any radial direction of the catheter.

Catheters having deflecting tips are also shown in U.S. Pat. No. 5,125,896 and European Patent Publication No. 361,314 (No. 9301018). In such catheters, a pull wire is included within the body of the catheter. When such wire is pulled, the distal end portion of the catheter bends in a somewhat arcuate manner. However, this deflection is not directly controlled or easily adjustable. In addition, when electrodes are included in these types of catheters, they are typically in the form of tip electrodes or ring electrodes that require generally conventional assembly arrangements.

The invention provides a controlled flexible catheter wherein the deflection always takes place in the same, known radial direction, so that for instance an electrode situated on the side of the catheter can be manipulated carefully into a desired position, for instance touching the wall of a blood vessel or of the heart. With the catheter according to the invention, this is achieved by fixing a pull wire, extending through the catheter in a secure manner. Preferably, the pull wire is fixed eccentrically, and the distal end portion of the catheter bends towards the side where the pull wire is fixed when the pull wire is pulled. Typically, the pull wire can be manufactured in a simple fashion and is securely engaged in a reliable manner within the end portion of the catheter, such as in a hook-like manner.

In an important aspect of the invention, a comparatively stiff sliding wire stiffens the distal end portion into which it extends, so that bending occurs at substantially only that part of the distal end portion into which the sliding wire does not extend. Advancing or withdrawing movement of the sliding wire adjusts the shape and length of the deflecting distal portion to the amount desired by the physician.

The invention is especially suitable for use with a strip-shaped electrode and/or heating element extending longitudinally in the wall of the flexible distal end portion of the catheter. Because of the controlled deflection of the distal end portion of the catheter, the entire length of this strip-shaped electrode can be placed carefully, for example against the wall of a ventricle, in order to locally heat and/or ablate tissue when treating certain types of cardiac arrhythmias. To assure adequate flexibility of the distal end portion of the catheter, the strip-shaped electrode assembly includes a helically wound wire which is very pliable and forms the strip-shaped electrode by means of the adjoining, uncovered windings of the strip-shaped electrode. A lateral side of this helically wound wire is situated at the surface of the end-section of the catheter to generally define the strip-shaped electrode.

It is a general object of this invention to provide an improved controlled flexible catheter.

Another object of the present invention is to provide an improved controlled catheter which achieves controlled flexing of its distal tip portion in an adjustable manner.

Another object of this invention is to provide an improved controlled flexible catheter which can be manipulated into a specific position, such as to orient an electrode thereof directly onto a desired location of a vessel wall or chamber.

Another object of the present invention is to provide an improved controlled flexible catheter by which proper and careful manipulation of the catheter is achieved by having a physician hold its proximal-end handle in one hand and operate a control assembly with a few fingers of the same hand.

Another object of this invention is to provide an improved controlled flexible catheter that exhibits a strip-like electrode which is an integral portion of a helically wound wire.

Another object of the present invention is to provide an improved controlled flexible catheter utilizing a pull wire which is securely and simply affixed at its distal end.

These and other objects, features and advantages of this invention will be clearly understood through a consideration of the following detailed description.

BRIEF DESCRIPTION OF THE DRAWINGS

The invention will be further elucidated in the following description with reference to the drawings in which:

FIG. 5 is a partly schematic generally perspective view of a catheter according to a further embodiment;

FIG. 6 is a cross-sectional view along the line VI—VI of FIG. 5;

FIG. 7 is a cross-sectional view along the line VII—VII of FIG. 5;

FIG. 8 is a partly broken away perspective view of a preferred control handle for a catheter according to the invention;

DESCRIPTION OF THE PARTICULAR EMBODIMENTS

Figure 1:
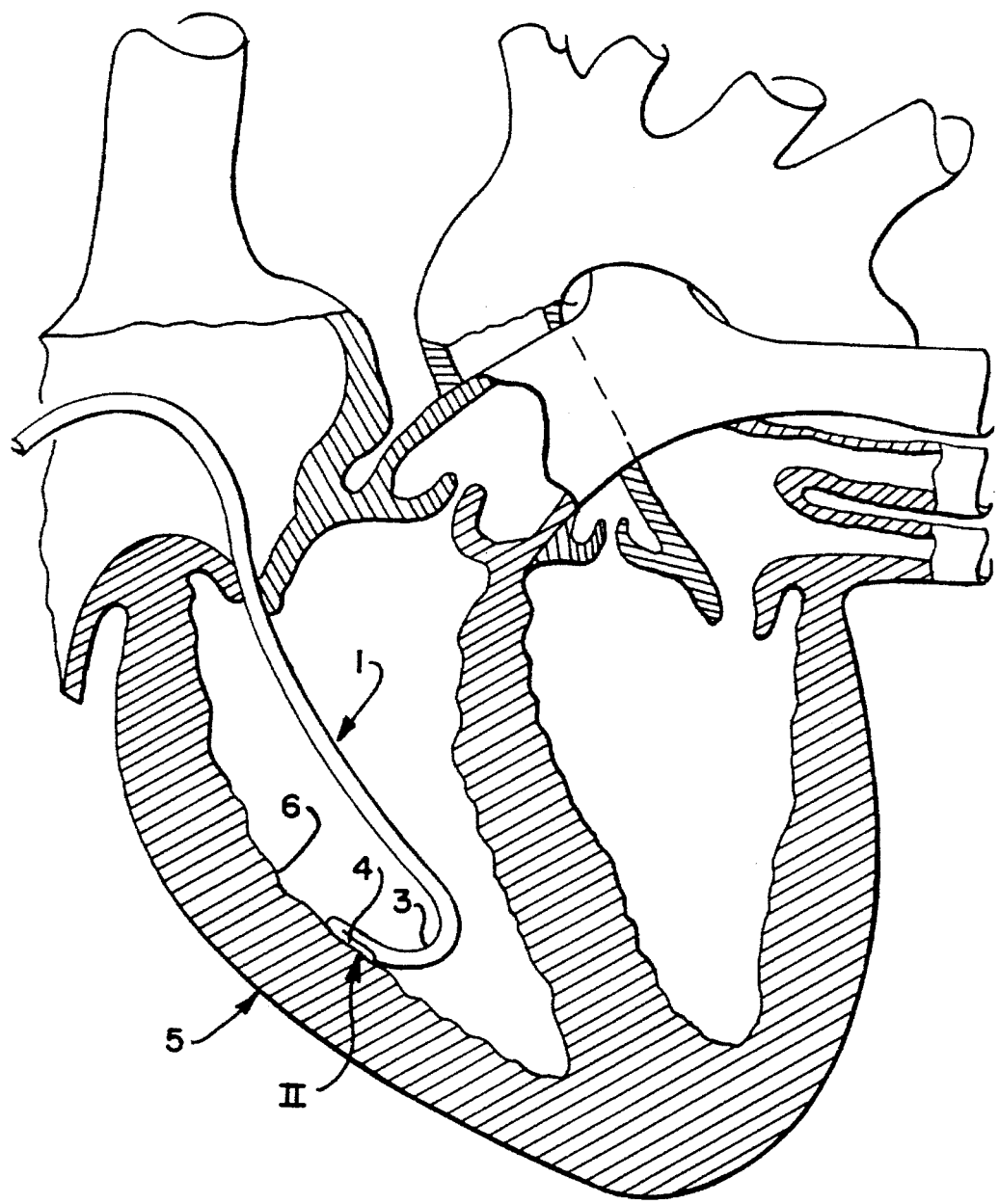
FIG. 1 is an illustration, generally in cross-section, of a catheter according to the invention in the position of use.

As FIG. 1 shows, a catheter according to the invention, generally designated at 1, can be advanced in the usual manner through a vein to the right ventricle in order to be positioned through a vein against the wall 6 of the right ventricle of the heart, generally designated at 5.

The catheter 1 includes an elongated body portion having a proximal end portion with a handle assembly or hub assembly. A connecting piece or member such as a connecting member 41 in FIG. 8 helps to secure the handle and/or hub assembly to the proximal portion of the catheter, which connecting piece or member typically remains outside the body during use. Catheter 1 also has a distal end portion having a flexible end section 3.

Typically, the wall of the flexible distal end portion or section is provided with a strip-like electrode, such as electrode 4, extending in the longitudinal direction of the catheter and positioned generally at the surface of the distal end portion. Such a strip-shaped electrode surface can function as a heating element for carrying out desired procedures.

The catheter 1 is, according to the invention, manufactured in such a way that its distal portion end section 3 can be bent reliably in a controlled fashion in order to place electrode 4 or other similarly positioned electrode firmly against the wall 6 of the vessel being treated or diagnosed. When the electrode is a heating element, a selected section of the wall 6 can be heated in this way and consequently the tissue disturbed intentionally so as to be useful, for example, when treating certain types of cardiac arrhythmias.

Figure 2:
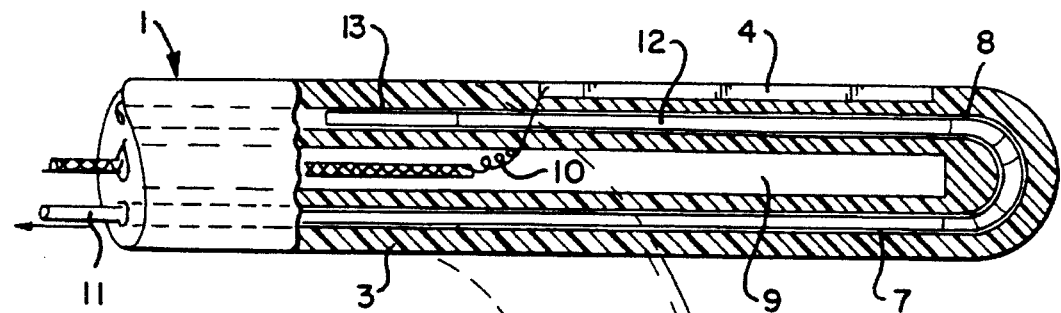
FIG. 2 is an elevational view, partially in cross-section of a distal end portion, designated at II in FIG. 1, of a catheter according to an embodiment of the invention.

As FIG. 2 shows in greater detail, the catheter 1 is provided with an eccentrically positioned channel 7; that is, this channel is radially offset from the central axis of the catheter body. Channel 7 accommodates a pull wire 11. This pull wire has been fixed in the distal end section 3. Preferably, this pull wire fixing is eccentric, such as by incorporating a doubled-up or folded-back end piece 12 of the pull wire 11 within a generally U-shaped cavity 8. When the catheter has a distal end section which is assembled to the body of the catheter, the pull wire end piece 12 may be placed against an end wall of the body of the catheter, at the position of the connection between the assembled flexible distal end section.

The pull wire 11 extends for the full length of the catheter 1 from the distal end, through the channel 7 and extends to at or near the proximal end outside the catheter. By pulling pull wire 11 from the proximal end of the catheter, the distal end section 3 of the catheter 1 bends in the direction that the channel 7 is radially offset from the catheter axis. A typical deflection in this regard is illustrated in phantom and is indicated by reference numeral 14.

In the embodiment illustrated in FIG. 2, the doubled-up distal end piece 12 of the pull wire 11 has been secured in cavity or channel 8 with adhesive or glue 13. Alternatively, when the distal end section 3 is a separate end section which is assembled into the catheter 1, the doubled-back end piece 12 of the pull wire can be placed against the end wall of the body portion of the catheter at the position of the connection between the distal end section and the body portion of the catheter.

FIG. 2 also shows a strip-like electrode at the distal end section. In this embodiment, the electrode is executed as heating element 4. A conductive connecting wire 10 runs through a channel 9, shown as following the longitudinal axis of the catheter, to the proximal end of the catheter where this connecting wire is connected to a suitable energy source.

In relation to the eccentrically positioned channel 7, the electrode 4 is placed at the radially opposite side of the catheter, so that this electrode 4 is always positioned on the outside curve of the catheter when it is bent by operation of the pull wire 11. This arrangement facilitates movement of the electrode firmly against the location of the vessel or body cavity which is to be subjected to diagnostic or treatment energy.

When desired, it would be also possible to place the electrode at the radially opposite side to that shown in FIG. 2, such as at a location close to the eccentrically located channel 7. In this type of an arrangement, the electrode would be positioned on the inside of the curved defined by manipulation of the pull wire 11.

Figure 3:
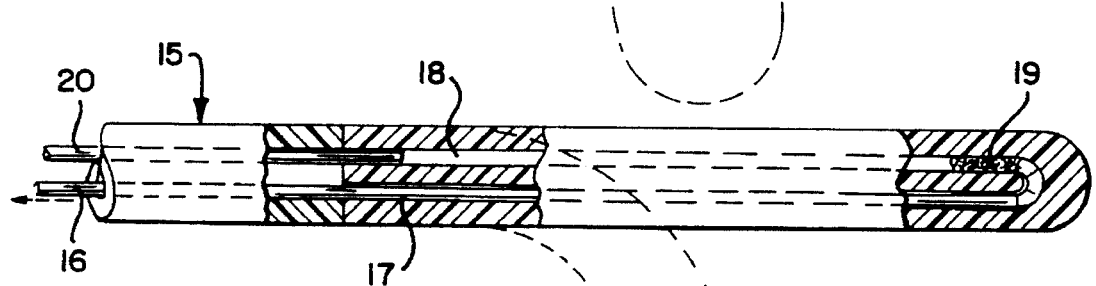
FIG. 3 is an elevational view, partially in cross-section of a distal end portion of another embodiment.

The catheter 15 shown in FIG. 3 also includes an eccentrically positioned channel 17 in the distal end section into which the pull wire 16 has been incorporated. The end of the pull wire has been doubled up over a distance 19 and within a distal portion of a channel 18 which is situated generally diametrically opposite the channel 17. Furthermore, the channel 18 extends the entire length of the distal end section. A movable sliding wire 20, which is comparatively stiff, is slidingly situated within this channel 18. With the position of the sliding wire 20 as shown in FIG. 3 the flexibility of the distal end section is not affected by, or affected only minimally by, the sliding wire 20, so that when the pull wire 16 is pulled, a deflection with a comparatively large bending radius is created. This large radius deflection 21 is illustrated in phantom in FIG. 3.

Figure 4:
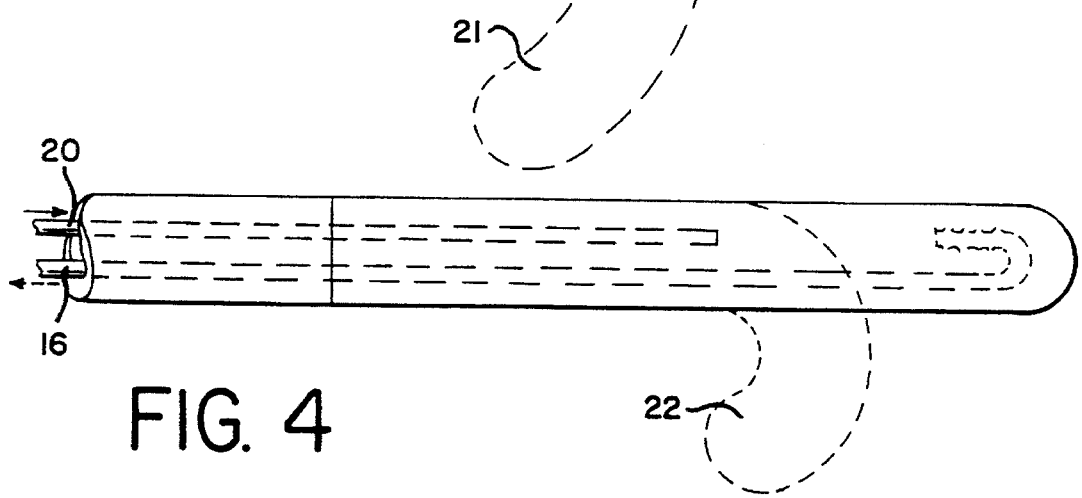
FIG. 4 is an elevational view of the catheter of FIG. 3 in another position of use.

When, as shown in FIG. 4, the sliding wire 20 is advanced further in the channel 18 in a distal direction, a deflection 22 with a much smaller radius will be formed when the pull wire 16 is advanced in the proximal direction. Basically, only that part of the distal end section will bend within which the sliding wire 20 is not situated.

In the embodiment illustrated in FIG. 5, catheter 25 is made up of a basic elongated body 26 and a flexible distal end section 27. As FIG. 6 and FIG. 7 show, both in the basic body 26 and the distal end section 27 have four channels therewithin. The bottom channel shown in the orientation illustrated in FIG. 6 and in FIG. 7 accommodates a pull wire 28 which is, as described above, fixed eccentrically with a doubled up distal end piece within the distal end section and at a location very close to the tip of the catheter 25.

Channel 29 of this embodiment is used for the supply of a contrast medium close to the tip of the catheter, so that the area surrounding the catheter can be made visible on an X-ray screen in a catheterization laboratory. The contrast substance conveyed can be delivered through holes such as hole 30.

The distal end section 27 is in this case provided with a strip-like electrode 32, which has been formed by the lateral surface 33 of a helically wound wire embedded in the material making up the basic elongated catheter body. Connecting wire 31 has been fed to the proximal end through the upper channel of the basic elongated body at the orientation shown in FIGS. 5, 6 and 7.

By manufacturing the electrode 32 in the form of a helically wound wire, the latter is very flexible and also to some extent elastic and easily stretched. In this way, the electrode components do not adversely affect the flexibility of the distal end section 27 of the catheter. The fourth channel 34 in the illustrated embodiment of FIGS. 5, 6 and 7 can be used for passage of a guidewire therethrough.

FIG. 8 represents a control assembly, generally designated 40, which can be used with a catheter 42 according to the invention. The catheter together with the pull wire, and if desired the sliding wire, is connected to the right hand side of the control assembly 40 by means of a connecting member 41 or the like. The catheter 42 is connected firmly to the control assembly 40.

The control assembly 40 includes a handle 48 and a sleeve or case 43 which is rotatable in relation to the handle 48. By means of a threaded joint 49, the handle 48 is screwed onto a basic element allowing the sleeve or case 43 to rotate. This basic body and the handle 48 comprise a continuous channel through which various components or materials can be fed, such as connecting wires for a heating element, a sliding wire, a guidewire, a contrast medium line and the like. A tangential channel 44 is connected to this central channel through which the pull wire 45 has been threaded. The pull wire 45 is connected securely to the case 43. As a result, when the case 43 is turned or rotated so the secure connection moves away from the tangential channel, the pull wire 45 is pulled in a proximal direction in order to curve the distal end section.

Preferably, a rubber ring 46 is positioned along the sleeve or case 43 so as to cause friction against rotation of the sleeve or case 43 to such an extent that the latter remains fixed in a particular chosen position of rotation. Also, the outside surface of the sleeve or case 43 preferably is provided with a roughened or milled surface ensuring a good grip.

In operation, the physician using the catheter with the control assembly 40 holds the control assembly at the handle 48 and can readily rotate the sleeve or case 43 with the thumb and index finger. Bending of the distal end section can thus be operated in a carefully controlled manner. Thus, proper and careful manipulation of the catheter according to the invention can be achieved by having a physician hold the handle in one hand and operate the control assembly with a few digits of the same hand. The rotatable sleeve can be operated with the thumb and index finger, while the handle is held with the other fingers. Transmission of the rotational movement of the sleeve to longitudinal movement of the pull wire is effected in a very simple and reliable manner and which incurs relatively low manufacturing costs.

In addition, a second relatively rotatable sleeve or case 43a can be included. It can be arranged to operate in substantially the same manner as sleeve or case 43 in order to effect sliding longitudinal movement of the sliding wire 20 by rotational movement of the second sleeve or case 43a. Thus, when provided, the second sleeve or case 43a will typically be manipulated first in order to adjust to the desired bending length, after which the first sleeve or case 43 will be manipulated or rotated in order to effect the desired depth of bending or curvature.

Figure 9:
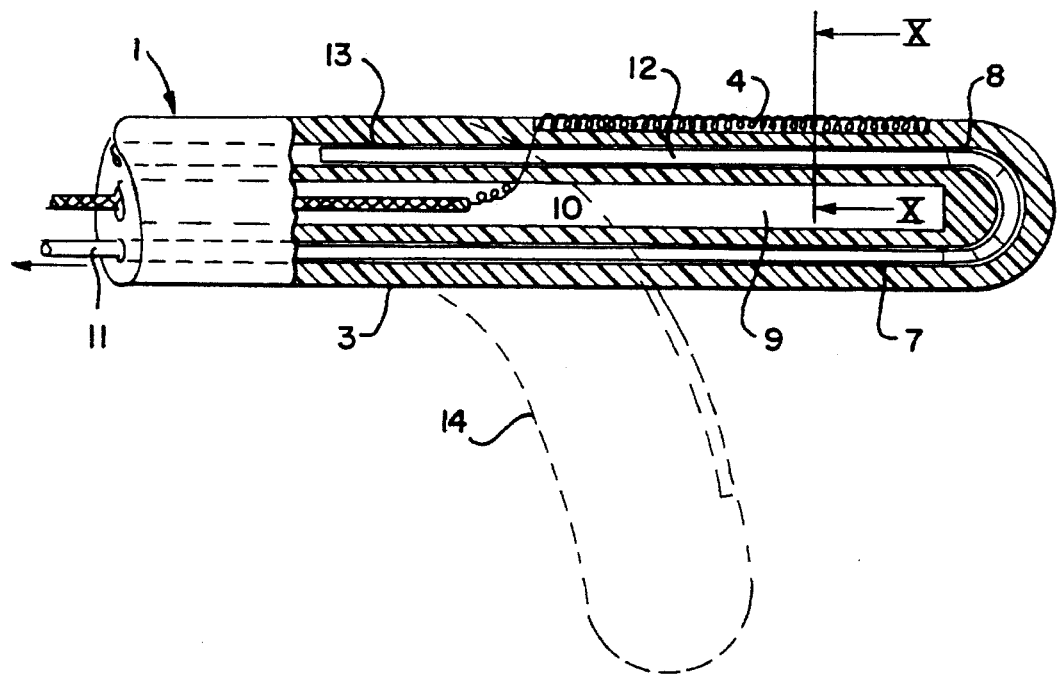
FIG. 9 is an elevational view, generally in cross-section, of a distal portion generally as shown in FIG. 2, of an embodiment of the invention.
Figure 10:
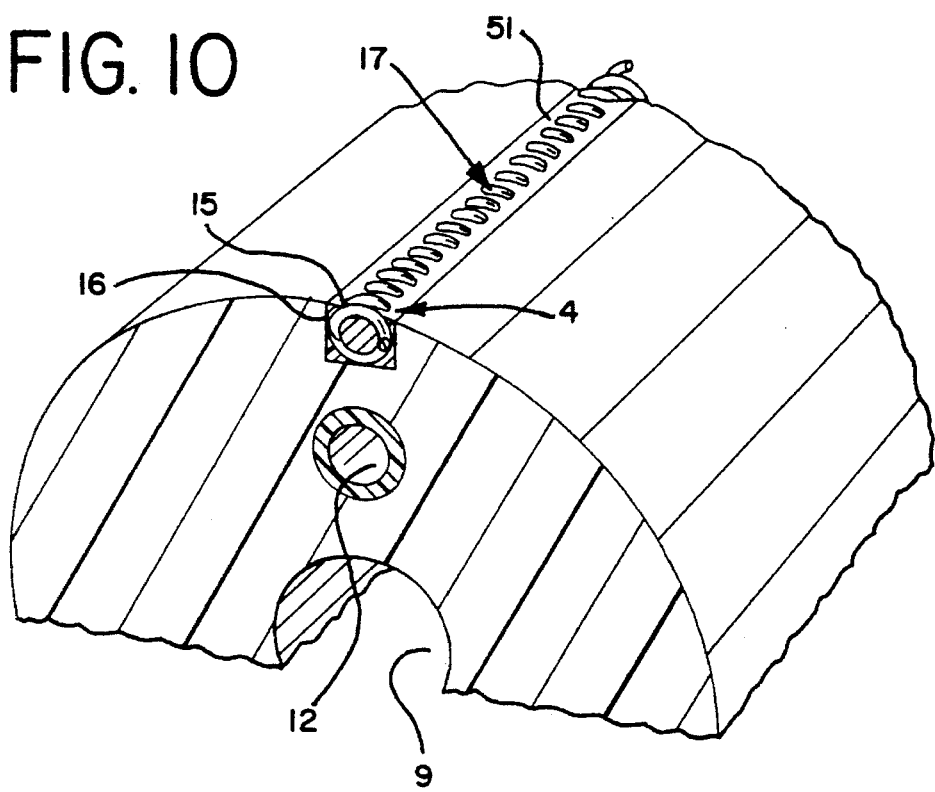
FIG. 10 is a cross-sectional perspective view along the line X—X of FIG. 9.

FIG. 9 and FIG. 10 show more in detail a preferred strip-like electrode 4 according to the invention. A helically wound wire 15 is incorporated in a slot or longitudinally extending depression 16 in the proximal end section. The depression 16 preferably has a depth somewhat shallower or smaller than the diameter of the wound wire 15. Accordingly, a lateral surface portion 17 of the wire is exposed at the outside of the catheter and forms the active surface of the electrode. The helically wound wire 15 preferably is fixed in the depression 16 by means of a suitable filling adhesive 51.

In another embodiment, the depression can have a depth equal to the diameter of the wound coil of wire. After embedding the wound wire in the depression 16, the outer surface of the end section of the catheter is ground or polished, so as to expose the lateral surface portion of the wound wire which becomes the active surface of the electrode.

It will be understood that the embodiments of the present invention which have been described are illustrative of some of the applications of the principles of the present invention. Various modifications may be made by those skilled in the art without departing from the true spirit and scope of the invention.

I claim:

1. A controlled flexible catheter, comprising:

an elongated body component having a proximal end and a generally tubular configuration and at least one continuous longitudinal channel therethrough;

a distal end portion at a distal end location of the body component and made of a generally tubular and flexible material and having at least one longitudinal passageway which is substantially coextensive with said continuous longitudinal channel of the elongated body component;

a pull wire slidably positioned within said longitudinal channel and said longitudinal passageway, said pull wire being anchored at a location of said distal end portion and being slidably manipulatable from a proximal location of the catheter;

a sliding wire slidably positioned along said elongated body component and said distal end portion, said sliding wire having a distal portion, said sliding wire being movable by manipulation from a proximal location of the catheter so that the location of its said distal portion is adjustable generally along the length of said distal end portion of the catheter;

said pull wire and said sliding wire cooperate to effect a generally curved bending of said distal end portion, the sliding wire primarily controlling the length of said distal end portion which is subjected to said bending, and the pull wire primarily controlling the extent of curvature of said length of the distal end portion which is subjected to said bending; and said sliding wire has a stiffness greater than that of said pull wire.

2. The catheter in accordance with claim 1, wherein at least a portion of said longitudinal passageway of the distal end portion is radially spaced from the central axis of the distal end portion, and said location at which the pull wire is anchored is an eccentric attachment location.

3. The catheter in accordance with claim 2, wherein said distal portion of the sliding wire is radially offset from the central axis of the distal end portion of the catheter in a direction generally opposite to the eccentric attachment location of the pull wire.

4. The catheter in accordance with claim 3, wherein said distal end portion of the sliding wire is diametrically opposite to said eccentric attachment location of the pull wire.

5. The catheter in accordance with claim 1, wherein said sliding wire is slidably positioned within a longitudinal channel and longitudinal passageway which is separate from the longitudinal channel and longitudinal passageway within which the pull wire is slidably positioned.

6. The catheter in accordance with claim 2, wherein said distal end portion includes a generally U-shaped passageway that is substantially co-extensive with said longitudinal passageway to define an eccentrically positioned passageway, said pull wire extending into said eccentrically positioned passageway, and the pull wire is doubled back in hook-shaped fashion at its distal end length.

7. The catheter in accordance with claim 1, further including a control assembly secured to the proximal end of the elongated body component, said control assembly including a handle and an operating member that is rotatable with respect to said handle, said elongated body component being attached to said handle, and said pull wire being attached to said operating member.

8. The catheter in accordance with claim 7, wherein said operating member is a sleeve that is rotatable around the handle, and said pull wire is threaded into said handle and attached to said sleeve by way of a generally tangential channel of said sleeve.

9. The catheter in accordance with claim 7, wherein said control assembly further includes a further operating member which is movable with respect to said handle, and said sliding wire is attached to said further operating member.

10. The catheter in accordance with claim 9, wherein said further operating member is rotatable with respect to said handle independently of rotation of said operating member of the pull wire.

11. The catheter in accordance with claim 1, further including a strip-like electrode along the external surface of the distal end portion of the catheter, said strip-like electrode extending in a longitudinal direction of the catheter, and an elongated conductor joins said strip-like electrode with the proximal end of the catheter.

12. The catheter in accordance with claim 11, wherein said strip-like electrode includes a helically wound wire incorporated within a longitudinal depression of said distal end portion of the catheter, said helically wound wire having a defined outside diameter, and said depression having a depth approximating said outside diameter of the helically wound coil.

13. The catheter in accordance with claim 12, wherein said depression depth is not greater than said outside diameter of the helically wound coil.

14. The catheter in accordance with claim 11, wherein said strip-like electrode defines a heating element.

15. A controlled flexible catheter, comprising:

an elongated body component having a proximal end and a generally tubular configuration and at least one continuous longitudinal channel therethrough;

a distal end portion at a distal end location of the body component and made of a generally tubular and flexible material and having at least one longitudinal passageway which is substantially coextensive with said continuous longitudinal channel of the elongated body component;

an elongated conductor positioned within said longitudinal channel and longitudinal passageway and extending from the proximal end of the catheter to the distal end portion;

a strip-like electrode extending from said elongated conductor and located along the distal end portion and in a longitudinal direction with respect to the catheter; and a bending assembly for effecting bending of said distal end portion, and said elongated conductor and strip-like electrode accommodate bending of said distal end portion by said bending assembly.

16. The conductor in accordance with claim 15, wherein said strip-like electrode includes a helically wound wire.

17. The catheter in accordance with claim 15, wherein said strip-like electrode includes a helically wound wire incorporated within a longitudinal depression of said distal end portion of the catheter, said helically wound wire having a defined outside diameter, and said depression having a depth approximating said outside diameter of the helically wound coil.

18. The catheter in accordance with claim 17, wherein said depression depth is not greater than said outside diameter of the helically wound coil.

19. The catheter in accordance with claim 15, wherein said strip-like electrode defines a heating element.

20. The catheter in accordance with claim 15, wherein said bending assembly includes a pull wire slidably positioned along the catheter and anchored at a location of said distal end portion, said pull wire being manipulatable from a proximal location of the catheter, and said location at which the pull wire is anchored is spaced radially from the central axis of the catheter.

21. The catheter in accordance with claim 15, further including a control assembly secured to the proximal end of the elongated body component, said control assembly including a handle and an operating member that is rotatable with respect to said handle, said elongated body component being attached to said handle, and said pull wire being attached to said operating member.

22. The catheter in accordance with claim 21, wherein said operating member is a sleeve that is rotatable around the handle, and said pull wire is threaded into said handle and attached to said sleeve by way of a generally tangential channel of said sleeve.

23. A controlled flexible catheter, comprising:

an elongated body component having a proximal end and a generally tubular configuration and at least one continuous longitudinal channel therethrough;

a distal end portion at a distal end location of the body component and made of a generally tubular and flexible material and having at least one longitudinal passageway which is substantially coextensive with said continuous longitudinal channel of the elongated body component;

a pull wire slidably positioned within said longitudinal channel and said longitudinal passageway, said pull wire being anchored at a location of said distal end portion and being slidably manipulatable from a proximal location of the catheter;

a sliding wire slidably positioned along said elongated body component and said distal end portion, said sliding wire having a distal portion, said sliding wire being movable by manipulation from a proximal location of the catheter so that the location of its said distal portion is adjustable generally along the length of said distal end portion of the catheter;

said pull wire and said sliding wire cooperate to effect a generally curved bending of said distal end portion, the sliding wire primarily controlling the length of said distal end portion which is subjected to said bending, and the pull wire primarily controlling the extent of curvature of said length of the distal end portion which is subjected to said bending;

at least a portion of said longitudinal passageway of the distal end portion is radially spaced from the central axis of the distal end portion, and said location at which the pull wire is anchored is an eccentric attachment location; and said distal end portion includes a generally U-shaped passageway that is substantially co-extensive with said longitudinal passageway to define an eccentrically positioned passageway, said pull wire extending into said eccentrically positioned passageway, and the pull wire is doubled back in hook-shaped fashion at its distal end length.

24. The catheter in accordance with claim 23, wherein said distal portion of the sliding wire is radially offset from the central axis of the distal end portion of the catheter in a direction generally opposite to the eccentric attachment location of the pull wire.

25. The catheter in accordance with claim 24, wherein said distal end portion of the sliding wire is diametrically opposite to said eccentric attachment location of the pull wire.

26. The catheter in accordance with claim 24, wherein said sliding wire is slidably positioned within a longitudinal channel and longitudinal passageway which is separate from the longitudinal channel and longitudinal passageway within which the pull wire is slidably positioned.

* * * * *